US006414034B1

(12) United States Patent
Reddy et al.

(10) Patent No.: US 6,414,034 B1
(45) Date of Patent: Jul. 2, 2002

(54) Z-STYRYL SULFONE TREATMENT OF PROLIFERATIVE DISEASES

(75) Inventors: E. Premkumar Reddy, Villanova; M. V. Ramana Reddy, Upper Darby, both of PA (US)

(73) Assignee: Temple University of the Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 09/722,450

(22) Filed: Nov. 22, 2000

Related U.S. Application Data

(62) Division of application No. 09/282,855, filed on Mar. 31, 1999, now Pat. No. 6,201,154.

(51) Int. Cl.[7] .............................................. A61K 31/10

(52) U.S. Cl. ........................ 514/710; 514/708; 568/28

(58) Field of Search ................................ 514/708, 710; 568/28

(56) References Cited

U.S. PATENT DOCUMENTS

| | | | |
|---|---|---|---|
| 2,532,612 A | 12/1950 | Doumani | 260/609 |
| 3,185,743 A | 5/1965 | Combe et al. | |
| 3,418,101 A | 12/1968 | Buchholtz et al. | |
| 3,514,386 A | 5/1970 | Oswald et al. | 204/162 |
| 3,917,714 A | 11/1975 | Richmond | 260/607 A |
| 4,161,407 A | 7/1979 | Campbell | 96/114 |
| 4,386,221 A | 5/1983 | Hyatt et al. | 568/28 |
| 4,937,388 A | 6/1990 | Bushell et al. | 568/56 |
| 5,659,087 A | 8/1997 | Aikins et al. | 568/27 |
| 5,733,909 A * | 3/1998 | Black et al. | 514/238.8 |

OTHER PUBLICATIONS

CA:126:185889 abs of JP09003037, Jan. 7, 1997.*
CA:100:203574 abs of Arch Ophthalmol (Chicago) by Blumenkranz et al 102(4) pp598–604, 1984.*
CA:129:243204 abs of Circulation by Braun–Dullaeus et al 98(1) pp 82–89, 1998.*
CA:123:350274 abs of EP679399, Nov. 1995.*
Chem Abstract 126:185889h, vol. 126 (14) (Apr. 7, 1997), abstracting Japanese Pat Appl. 09–03,037 (Jan. 7, 1997).
D. Bhaskar Reddy, N.S. Reddy, S. Reddy, M.V.R. Reddy and S. Balasubramanyam, *Org. Prep. Proc. Int.*, 20:205–212 (1988).
D. Bhasker Reddy, P.V. Ramana Reddy, V. Padmavathi, and M.V. Ramana Reddy, *Sulfur Lett.*, 13(2):83–90 (1991).
M.V.R. Reddy and S. Reddy, *Acta Chim. Acad. Sci. Hung.*, 115:269–271 (1984).
M.V. Reddy, V. Vijayalakshmi, D. Bhaskar Reddy and P.V. Ramana Reddy, *Phosphorus, Sulfur Silicon Relat. Elem.*, 60:209–214 (1991).
M.V. Reddy and S. Reddy, *Acta Chim. Acad. Sci. Hung.*, 120(4):275–280 (1985).
M.V.R. Reddy and S. Reddy, *Synthesis* No. 4, 322–323 (1984).
M.V.R. Reddy, S. Reddy and D.B. Reddy, *Sulfur Lett.*, 7(2):43–48 (1987).
Reddy et al., "A New Route for the Synthesis of Styrylbenzylsulfones, Precursors of 1–Benzylsulfonyl–2–Arylcyclopropanes", *Phosphorus, Sulfur, and Silicon*, 53:285–290 (1990).
Mieczyslaw Makosza and Irina Krylova, "Some Reactions of the Chloromethyl trans–β–Styryl Sulfone Carbanion", *Liebigs Ann./Recueil*, pp. 2337–2340 (1997).
Reddy et al., "Phase Transfer Catalysis—A Facile Method for Cyclopropanation of Some Isomeric Styryl Benzyl Sulfones and Bis(Styryl)Sulfones", *Acta Chim. Hung.*, 131(1):83–92 (1994).
Database Caplus on STN, Chem Abstracts, (Columbus OH, USA) No. 124:175763, Reddy, D.B. et al., 'Synthesis of 1,1–disubstited, 2,6–diaryl–4–thian–4,4–dioxides, part–II' abstract Indian J. Heterocycl. Chem., May 1995, vol. 5, No. 1, pp. 11–14.
Database Caplus on STN, Chem. Abstracts, (Columbus OH, USA) No. 124:146025, Reddy, D.B. et al., 'E,Z and E,E–bis(styryl) sulfones as precursors of thiane oxides' abstract Indian J. Heterocycl. Chem. Apr. 1995, vol. 4, No. 4, pp. 259–264.

(List continued on next page.)

Primary Examiner—Jean F. Vollano
(74) Attorney, Agent, or Firm—Drinker Biddle & Reath LLP

(57) ABSTRACT

(Z)-styryl benzylsulfones of formula I are useful as anticancer agents:

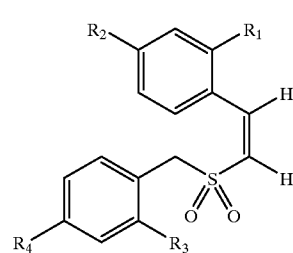

wherein
  $R_1$ is selected from the group consisting of hydrogen, chloro and nitro;
  $R_2$ is selected from the group consisting of hydrogen, lower alkyl, lower alkoxy, chloro, bromo, and fluoro; and
  $R_3$ and $R_4$ are independently selected from the group consisting of hydrogen, lower alkyl, nitro, chloro, bromo, and fluoro;
  provided that at least one of $R_1$ or $R_2$ is hydrogen.
The corresponding (Z)-styryl benzylsulfides are useful as intermediates in the preparation of the biologically active (Z)-styryl benzyl sulfones.

22 Claims, No Drawings

OTHER PUBLICATIONS

CA:100:67921, abstracting Takikawa, et al., *Chem. Lett.* (9):1351–4, 1983.

CA:121:156180, abstracting Li, et al., *Bioorg. Med. Chem. Lett.* 4(13):1585–90, 1994.

CA:120:323356, abstracting Reddy et al., *Sulfur Lett.* 16(5–6):227–35, 1993.

CA:76:121420, abstracting Findlay et al., *Brit. J. Dermatol.,* Suppl. (7):44–9, 1971.

CA:124:8731, abstracting Reddy et al., *Indian J. Chem., Sect. B: Org. Chem. Incl. Med. Chem.* 34B(9):816–22, 1995.

CA:122:132682, abstracting Reddy et al., *Phosphorus, Sulfur Silicon Relat. Elem.* 90 (1–4):1–10, 1994.

CA:105:133446, abstracting Naidu et al., *Proc.—Indian Acad. Sci., Chem. Sci.* 95(4):391–5, 1985.

CA:121:34425, abstracting Benati et al, *J. Org. Chem* 59(10) 2818–2823, 1994.

CA:128:48012, abstracting Mokosza et al., *Liebigs Ann./Recueil,* 2337–2340, 1997.

CA:130:281870, abstracting WO 9918068 (Apr. 1999).

CA:121:255346, abstracting Reddy, et al., *Acta Chim. Hung.* 131(I): 83–92 (1994).

CA:101:23063 abstracting Reddy, et al., *Acta Chim Hung.* 115(3) 269–271, 1984.

\* cited by examiner

Z-STYRYL SULFONE TREATMENT OF PROLIFERATIVE DISEASES

This is a divisional of application Ser. No. 09/282,855 filed Mar. 31, 1999, now U.S. Pat. No. 6,201,154.

FIELD OF THE INVENTION

The invention relates to compositions and methods for the treatment of cancer.

BACKGROUND OF THE INVENTION

Extracellular signals received at transmembrane receptors are relayed into the cells by the signal transduction pathways (Pelech et al., *Science* 257:1335 (1992)) which have been implicated in a wide array of physiological processes such as induction of cell proliferation, differentiation or apoptosis (Davis et al., *J. Biol. Chem.* 268:14553 (1993)). The Mitogen Activated Protein Kinase (MAPK) cascade is a major signaling system by which cells transduce extracellular cues into intracellular responses (Nishida et al., *Trends Biochem. Sci.* 18:128 (1993); Blumer et al., *Trends Biochem. Sci.* 19:236 (1994)). Many steps of this cascade are conserved, and homologous for MAP kinases have been discovered in different species.

In mammalian cells, the Extracellular-Signal-Regulated Kinases (ERKs), ERK-1 and ERK-2 are the archetypal and best-studied members of the MAPK family, which all have the unique feature of being activated by phosphorylation on threonine and tyrosine residues by an upstream dual specificity kinase (Posada et al., *Science* 255:212 (1992); Biggs III et al., *Proc. Natl. Acad. Sci. USA* 89:6295 (1992); Garner et al., *Genes Dev.* 6:1280 (1992)).

Recent studies have identified an additional subgroup of MAPKs, known as c-Jun NH2-terminal kinases 1 and 2 (JNK-1 and JNK-2), that have different substrate specificities and are regulated by different stimuli (Hibi et al., *Genes Dev.* 7:2135 (1993)). JNKs are members of the class of stress-activated protein kinases (SPKs). JNKs have been shown to bectivated by treatment of cells with UV radiation, pro-inflammatory cytokines and environmental stress (Derijard et al., *Cell* 1025 (1994)). The activated JNK binds to the amino terminus of the c-Jun protein and increases the protein's transcriptional activity by phosphorylating it at ser63 and ser73 (Adler et al., *Proc. Natl. Acad. Sci. USA* 89:5341 (1992); Kwok et al., *Nature* 370:223 (1994)).

Analysis of the deduced primary sequence of the JNKs indicates that they are distantly related to ERKs (Davis, *Trends Biochem. Sci.* 19:470 (1994)). Both ERKs and JNKs are phosphorylated on Tyr and Thr in response to external stimuli resulting in their activation (Davis, *Trends Biochem. Sci.* 19:470 (1994)). The phosphorylation (Thr and Tyr) sites, which play a critical role in their activation are conserved between ERKs and JNKs (Davis, *Trends Biochem. Sci.* 19:470 (1994)). However, these sites of phosphorylation are located within distinct dual phosphorylation motifs: Thr-Pro-Tyr (JNK) and Thr-Glu-Tyr (ERK). Phosphorylation of MAPKs and JNKs by an external signal often involves the activation of protein tyrosine kinases (PTKs) (Gille et al., *Nature* 358:414 (1992)), which constitute a large family of proteins encompassing several growth factor receptors and other signal transducing molecules.

Protein tyrosine kinases are enzymes which catalyze a well defined chemical reaction: the phosphorylation of a tyrosine residue (Hunter et al., *Annu Rev Biochem* 54:897 (1985)). Receptor tyrosine kinases in particular are attractive targets for drug design since blockers for the substrate domain of these kinases is likely to yield an effective and selective antiproliferative agent. The potential use of protein tyrosine kinase blockers as antiproliferative agents was recognized as early as 1981, when quercetin was suggested as a PTK blocker (Graziani et al., *Eur. J. Biochem.* 135:583–589 (1983)).

The best understood MAPK pathway involves extracellular signal-regulated kinases which constitute the Ras/Raf/MEK/ERK kinase cascade (Boudewijn et al., *Trends Biochem. Sci.* 20, 18 (1995)). Once this pathway is activated by different stimuli, MAPK phosphorylates a variety of proteins including several transcription factors which translocate into the nucleus and activate gene transcription. Negative regulation of this pathway could arrest the cascade of these events.

What are needed are new anticancer chemotherapeutic agents which target receptor tyrosine kinases and which arrest the Ras/Raf/MEK/ERK kinase cascade. Oncoproteins in general, and signal transducing proteins in particular, are likely to be more selective targets for chemotherapy because they represent a subclass of proteins whose activities are essential for cell proliferation, and because their activities are greatly amplified in proliferative diseases.

SUMMARY OF THE INVENTION

It is an object of the invention to provide compounds, compositions and methods for the treatment of cancer and other proliferative diseases. The biologically active compounds are in the form of (Z)-styryl benzylsulfones.

It is a further object of the invention to provide intermediates useful for the preparation of compounds having anticancer activity. The intermediates comprise (Z)-styryl benzylsulfides.

The present invention provides for pharmaceutical compositions comprising a pharmaceutically acceptable carrier and one or more compounds of the formula I

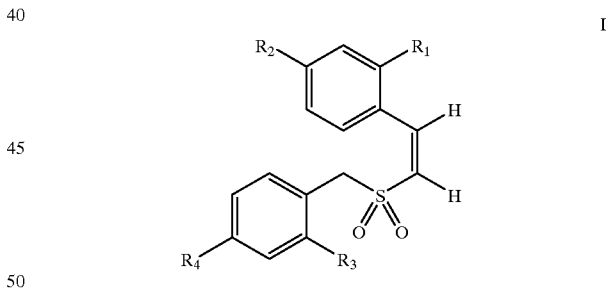

wherein $R_1$ is selected from the group consisting of hydrogen, chloro and nitro;

$R_2$ is selected from the group consisting of hydrogen, lower alkyl, lower alkoxy, chloro, bromo, and fluoro; and $R_3$ and $R_4$ are independently selected from the group consisting of hydrogen, lower alkyl, nitro, chloro, bromo, and fluoro;

provided at least one of $R_1$ or $R_2$ is hydrogen.

According to one preferred embodiment of the invention, pharmaceutical compositions of compounds of formula I are provided wherein $R_1$ is hydrogen. More preferably, $R_1$ and $R_3$ are hydrogen, and $R_2$ and $R_4$ are independently selected from the group consisting of chloro, fluoro and bromo.

According to another embodiment of the invention, novel compounds of formula I are provided where $R_1$, $R_2$, $R_3$ and $R_4$ are defined as above, provided:
(a) at least one of $R_1$ or $R_2$ is hydrogen;
(b) $R_3$ and $R_4$ may not both be hydrogen when:
(i) $R_1$ and $R_2$ are both hydrogen,
(ii) $R_1$ is chloro and $R_2$ is hydrogen, or
(iii) $R_2$ is chloro and $R_1$ is hydrogen; and
(c) when $R_3$ is hydrogen and $R_4$ is methyl:
(i) both $R_1$ and $R_2$ may not be hydrogen,
(ii) $R_1$ may not be chloro when $R_2$ is hydrogen, and
(iii) $R_2$ may not be chloro when $R_1$ is hydrogen.

Preferably, $R_1$ is hydrogen in the novel compounds of the invention.

According to another embodiment of the invention, novel (Z)-styryl benzylsulfides are provided which are useful as intermediates in the preparation of the biologically active (Z)-styryl benzylsulfones. The (Z)-styryl benzylsulfides have the formula:

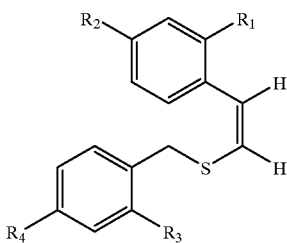

II wherein:
$R_1$ is selected from the group consisting of hydrogen, chloro and nitro;
$R_2$ is selected from the group consisting of hydrogen, lower alkyl, lower alkoxy, chloro, bromo, and fluoro, provided that at least one of $R_1$ or $R_2$ is hydrogen;
$R_3$ and $R_4$ are independently selected from the group consisting of hydrogen, lower alkyl, nitro, chloro, bromo, and fluoro; provided:
(a) at least one of $R_1$ or $R_2$ is hydrogen;
(b) $R_3$ and $R_4$ may not both be hydrogen when:
(i) $R_1$ and $R_2$ are both hydrogen,
(ii) $R_1$ is chloro and $R_2$ is hydrogen, or
(iii) $R_2$ is chloro and $R_1$ is hydrogen; and
(c) when $R_3$ is hydrogen and $R_4$ is methyl:
(i) both $R_1$ and $R_2$ may not be hydrogen,
(ii) $R_1$ may not be chloro when $R_2$ is hydrogen, and
(iii) $R_2$ may not be chloro when $R_1$ is hydrogen.

Preferably, $R_1$ is hydrogen in the aforementioned intermediates.

By "lower alkyl" is meant straight or branched chain alkyl containing from one to six carbon atoms. The preferred alkyl group is methyl. By "lower alkoxy" is meant straight or branched chain alkoxy containing from one to six carbon atoms. The preferred alkoxy group is methoxy.

According to another embodiment of the invention, a method of treating an individual for cancer or other proliferative disorder is provided, comprising administering to said individual an effective amount of the aforesaid pharmaceutical composition.

In another embodiment, a method of inhibiting growth of tumor cells in an individual afflicted with cancer is provided, comprising administering to said individual an effective amount of the aforesaid pharmaceutical composition.

In another embodiment, a method of inducing apoptosis of cancer cells, more preferably tumor cells, in an individual afflicted with cancer is provided, comprising administering to said individual an effective amount of the aforesaid pharmaceutical composition.

DETAILED DESCRIPTION OF THE INVENTION

According to the present invention, certain (Z)-styryl sulfone derivatives selectively kill various tumor cell types without killing normal cells. Without wishing to be bound by any theory, it is believed that the compounds affect the MAPK signal transduction pathway, thereby affecting tumor cell growth and viability. This cell growth inhibition is associated with regulation of the ERK and JNK types of MAPK.

The compounds of the invention have been shown to inhibit the proliferation of various tumor cells by inducing cell death. The compounds are effective against a broad range of tumor types, including but not limited to the following: breast, prostate, ovarian, lung, brain (i.e, glioma) and renal. The compounds are also effective against leukemic cells. The compounds do not kill normal cells in concentrations at which tumor cells are killed.

Treatment of this broad range of tumor cells with the styryl sulfone compounds of the invention leads to inhibition of cell proliferation and induction of apoptotic cell death. In breast tumors, the effect is observed for estrogen receptor (ER) positive as well as estrogen receptor negative cells.

Tumor cells treated with the compounds of the invention accumulate in the G2/M phase of the cell cycle. As the cells exit the G2/M phase, they appear to undergo apoptosis. Treatment of normal cells with the styryl sulfones does not result in apoptosis.

Both cells treated with the styryl sulfone compounds of the invention and untreated cells exhibit similar levels of intracellular ERK-2, but the biochemical activity of ERK-2, as judged by its ability to phosphorylate the substrate myelin basic protein (MBP), is considerably diminished in drug-treated cell compared to untreated cells. Without wishing to be bound by any theory, these results suggest that the styryl sulfones of the present invention block the phosphorylating capacity of ERK-2.

The styryl sulfones of the present invention enhance the ability of JNK to phosphorylate c-Jun protein compared to mock-treated cells. Without wishing to be bound by any theory, this result suggests that the styryl sulfones may be acting like pro-inflammatory cytokines or UV light, activating the JNK pathway, which in turn may switch on genes responsible for cell growth inhibition and apoptosis.

Synthesis of (Z)-Styryl Sulfones

The compounds of the present invention were prepared by synthetic methods yielding pure compounds in the (Z)-isomeric configuration. Thus, the nucleophilic addition of the appropriate thiols to substituted phenylacetylene with subsequent oxidation of the resulting sulfide by hydrogen peroxide yields the Z-styryl sulfone. The procedure is generally described by Reddy et al., *Sulfur Letters* 13:83 (1991), the entire disclosure of which is incorporated herein as a reference.

The compounds are named according to the Cahn-Ingold-Prelog system, the IUPAC 1974 Recommendations, Section E: stereochemistry, in *Nomenclature of Organic Chemistry*, Pergamon, Elmsford, N.Y., 1979 (the "Blue Book").

In the first step of the synthesis, the sodium salt of benzyl mercaptan or the appropriate substituted benzyl mercaptan is allowed to react with phenylacetylene or the appropriate substituted phenylacetylene forming the pure Z-isomer of the corresponding styryl benzylsulfide in good yield.

In the second step of the synthesis, the (Z)-styryl benzylsulfide intermediate is oxidized to the corresponding sulfone in the pure Z-isomeric form by treatment with hydrogen peroxide.

General Procedure for the Synthesis of (Z)-Styryl Benzylsulfones

A. Synthesis of Intermediate Sulfides

To a refluxing methanolic solution of substituted or unsubstituted sodiumbenzylthiolate prepared from 460 mg (0.02 g atom) of (i) sodium, (ii) substituted or unsubstituted benzyl mercaptan (0.02 mol) and (iii) 80 ml of absolute methanol, is added freshly distilled substituted or unsubstituted phenylacetylene. The mixture is refluxed for 20 hours, cooled and then poured on crushed ice. The crude product is filtered, dried and recrystalized from methanol or aqueous methanol to yield a pure (Z)-styryl benzylsulfide.

B. Synthesis of Sulfone

An ice cold solution of a (Z)-styryl benzylsulfide (3.0 g) in 30 ml of glacial acetic acid is treated with 7.5 ml of 30% hydrogen peroxide. The reaction mixture is refluxed for 1 hour and then poured on crushed ice. The separated solid is filtered, dried, and recrystalized from 2-propanol to yield the pure (Z)-styryl benzylsulfone. The purity of the compounds is ascertained by thin layer chromatography and geometrical configuration is assigned by analysis of infrared and nuclear magnetic resonance spectral data.

Therapeutic Administration

The styryl sulfones of the invention may be administered in the form of a pharmaceutical composition, in combination with a pharmaceutically acceptable carrier. The active ingredient in such formulations may comprise from 0.1 to 99.99 weight percent. By "pharmaceutically acceptable carrier" is meant any carrier, diluent or excipient which is compatible with the other ingredients of the formulation and to deleterious to the recipient.

The compounds of the invention may be administered to individuals (mammals, including animals and humans) afflicted with breast or prostate cancer. The compounds may be administered by any route, including oral and parenteral administration. Parenteral administration includes, for example, intravenous, intramuscular, intraarterial, intraperitoneal, intranasal, rectal, or subcutaneous administration. The active agent is preferably administered with a pharmaceutically acceptable carrier selected on the basis of the selected route of administration and standard pharmaceutical practice.

The active agent may be formulated into dosage forms according to standard practices in the field of pharmaceutical preparations. See Gennaro Alphonso, ed., *Remington's Pharmaceutical Sciences*, 18th Ed., (1990) Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil, saline solution, aqueous dextrose (glucose) and related sugar solutions, or a glycol such as propylene glycol or polyethylene glycol. Solutions for parenteral administration preferably contain a water soluble salt of the active agent. Stabilizing agents, antioxidizing agents and preservatives may also be added. Suitable antioxidizing agents include sulfite, ascorbic acid, citric acid and its salts, and sodium EDTA. Suitable preservatives include benzalkonium chloride, methyl- or propyl-paraben, and chlorbutanol.

For oral administration, the active agent may be combined with one or more solid inactive ingredients for the preparation of tablets, capsules, or other suitable oral dosage forms. For example, the active agent may be combined with carboxymethylcellulose calcium, magnesium stearate, mannitol and starch, and then formed into tablets by conventional tableting methods.

The specific dose of compound according to the invention to obtain therapeutic benefit will, of course, be determined by the particular circumstances of the individual patient including, the size, weight, age and sex of the patient, the nature and stage of the disease, the aggressiveness of the disease, and the route of administration. For example, a daily dosage of from about 0.05 to about 50 mg/kg/day may be utilized. Higher or lower doses are also contemplated.

The practice of the invention is illustrated by the following non-limiting examples.

EXAMPLE 1

Z-Styryl Benzylsulfone

A solution of phenylacetylene (0.02 mol) and benzyl mercaptan (0.02 mol) and metallic sodium (0.02 g atom) was subjected to the General Procedure, part A, to form Z-styryl benzylsulfide. The title compound was obtained in 65% yield by oxidation of the sulfide according to the General Procedure, part B. $^1$HNMR (CDCl$_3$) δ 4.50 (2H, s), 6.65 (1H, d, $J_{H,H}$=11.2), 7.18–7.74 (10H aromatic+1H ethylenic).

EXAMPLE 2

Z-Styryl 4-Chlorobenzylsulfone

A solution of phenylacetylene (0.02 mol) and 4-chlorobenzyl mercaptan (0.02 mol) and metallic sodium (0.02 g atom) was subjected to the General Procedure to form Z-styryl 4-chlorobenzylsulfide. The title compound was obtained in 72% yield following oxidation. $^1$HNMR (CDCl$_3$) δ 4.56 (2H, s), 6.68 (1H, d, $J_{H,H}$=11.8), 7.20–7.64 (9H aromatic+1H ethylenic).

EXAMPLE 3

Z-Styryl 2-Chlorobenzylsulfone

A solution of phenylacetylene (0.02 mol) and 2-chlorobenzyl mercaptan (0.02 mol) and metallic sodium (0.02 g atom) was subjected to the General Procedure to form Z-styryl 2-chlorobenzylsulfide. The title compound was obtained in 68% yield following oxidation. $^1$HNMR (CDCl$_3$) δ 4.50 (2H, s), 6.65 (1H, d, $J_{H,H}$=12.0), 7.18–7.74 (9H aromatic+1H ethylenic).

EXAMPLE 4

Z-Styryl 4-Fluorobenzylsulfone

A solution of phenylacetylene (0.02 mol) and 4-fluorobenzyl mercaptan (0.02 mol) and metallic sodium (0.02 g atom) was subjected to the General Procedure to from Z-styryl 4-fluorobenzylsulfide. The title compound was obtained in 70% yield following oxidation. $^1$HNMR (CDCl$_3$) δ 4.58 (2H, s), 6.62 (1H, d, $J_{H,H}$=11.86), 7.18–7.60 (9H aromatic+1H ethylenic).

EXAMPLE 5

Z-4-Chlorostyryl Benzylsulfone

A solution of 4-chlorophenylacetylene (0.02 mol) and benzyl mercaptan (0.02 mol) and metallic sodium (0.02 g atom) was subjected to the General Procedure to form Z-4-chlorostyryl benzylsulfide. The title compound was obtained in 74% yield following oxidation. $^1$HNMR (CDCl$_3$) δ 4.55 (2H, s), 6.66 (1H, d, $J_{H,H}$=12.12), 7.16–7.65 (9H aromatic+1H ethylenic).

EXAMPLE 6

Z-4-Chlorostyryl 4-Chlorobenzylsulfone

A solution of 4-chlorophenylacetylene (0.02 mol) and 4-chlorobenzyl mercaptan (0.02 mol) and metallic sodium (0.02 g atom) was subjected to the General Procedure to form Z-4-chlorostyryl 4-chlorobenzylsulfide. The title compound was obtained in 76% yield following oxidation. $^1$HNMR (CDCl$_3$) δ 4.62 (2H, s), 6.68 (1H, d, $J_{H,H}$=11.92), 7.18–7.60 (8H aromatic+1H ethylenic).

EXAMPLE 7

Z-4-Chlorostyryl 2-Chlorobenzylsulfone

A solution of 4-chlorophenylacetylene (0.02 mol) and 2-chlorobenzyl mercaptan (0.02 mol) and metallic sodium (0.02 g atom) was subjected to the General Procedure to form Z-4-chlorostyryl 2-chlorobenzylsulfide. The title compound was obtained in 73% yield following oxidation. $^1$HNMR (CDCl$_3$) δ 4.56 (2H, s), 6.70 (1H, d, $J_{H,H}$=12.05), 7.18–7.64 (8H aromatic+1H ethylenic).

EXAMPLE 8

Z-4-Chlorostyryl 4-Fluorobenzylsulfone

A solution of 4-chlorophenylacetylene (0.02 mol) and 4-fluorobenzyl mercaptan (0.02 mol) and metallic sodium (0.02 g atom) was subjected to the General Procedure to form Z-4-chlorostyryl 4-fluorobenzylsulfide. The title compound was obtained in 82% yield following oxidation. $^1$HNMR (CDCl$_3$) δ 4.60 (2H, s), 6.70 (1H, d, $J_{H,H}$=11.78), 7.18–7.60 (8H aromatic+1H ethylenic).

EXAMPLE 9

Z-4-Fluorostyryl Benzylsulfone

A solution of 4-fluorophenylacetylene (0.02 mol) and benzyl mercaptan (0.02 mol) and metallic sodium (0.02 g atom) was subjected to the General Procedure to form Z-4-fluorostyryl benzylsulfide. The title compound was obtained in 76% yield following oxidation. $^1$HNMR (CDCl$_3$) δ 4.54 (2H, s), 6.68 (1H, d, $J_{H,H}$=11.94), 7.12–7.58 (9H aromatic+1H ethylenic).

EXAMPLE 10

Z-4-Fluorostyryl 4-Chlorobenzylsulfone

A solution of 4-fluorophenylacetylene (0.02 mol) and 4-chlorobenzyl mercaptan (0.02 mol) and metallic sodium (0.02 g atom) was subjected to the General Procedure to form Z-4-fluorostyryl 4-chlorobenzylsulfide. The title compound was obtained in 82% yield following oxidation. $^1$HNMR (CDCl$_3$) δ 4.60 (2H, s), 6.68 (1H, d, $J_{H,H}$=11.84), 7.18–7.60 (8H aromatic+1H ethylenic).

EXAMPLE 11

Z-4-Fluorostyryl 2-Chlorobenzylsulfone

A solution of 4-fluorophenylacetylene (0.02 mol) and 2-chlorobenzyl mercaptan (0.02 mol) and metallic sodium (0.02 g atom) was subjected to the General Procedure to form Z-4-fluorostyryl 2-chlorobenzylsulfide. The title compound was obtained in 74% yield following oxidation. $^1$HNMR (CDCl$_3$) δ 4.55 (2H, s), 6.66 (1H, d, $J_{H,H}$=11.94), 7.20–7.65 (8H aromatic+1H ethylenic).

EXAMPLE 12

Z-4-Fluorostyryl 4-Fluorobenzylsulfone

A solution of 4-fluorophenylacetylene (0.02 mol) and 4-fluorobenzyl mercaptan (0.02 mol) and metallic sodium (0.02 g atom) was subjected to the General Procedure to form Z-4-fluorostyryl 4-fluorobenzylsulfide. The title compound was obtained in 78% yield following oxidation. $^1$HNMR (CDCl$_3$) δ 4.60 (2H, s), 6.65 (1H, d, $J_{H,H}$=11.83), 7.20–7.65 (8H aromatic+1H ethylenic).

EXAMPLE 13

Z-4-Bromostyryl Benzylsulfone

A solution of 4-bromophenylacetylene (0.02 mol) and benzyl mercaptan (0.02 mol) and metallic sodium (0.02 g atom) was subjected to the General Procedure to form Z-4-bromostyryl benzylsulfide. The title compound was obtained in 80% yield following oxidation. $^1$HNMR (CDCl$_3$) δ 4.52 (2H, s), 6.80 (1H, d, $J_{H,H}$=11.98), 7.18–7.59 (9H aromatic+1H ethylenic).

EXAMPLE 14

Z-4-Bromostyryl 4-Chlorobenzylsulfone

A solution of 4-bromophenylacetylene (0.02 mol) and 4-chlorobenzyl mercaptan (0.02 mol) and metallic sodium (0.02 g atom) was subjected to the General Procedure to form Z-4-bromostyryl 4-chlorobenzylsulfide. The title compound was obtained in 87% yield following oxidation. $^1$HNMR (CDCl$_3$) δ 4.58 (2H, s), 6.72 (1H, d, $J_{H,H}$=12.08), 7.15–7.68 (8H aromatic+1H ethylenic).

EXAMPLE 15

Z-4-Bromostyryl 2-Chlorobenzylsulfone

A solution of 4-bromophenylacetylene (0.02 mol) and 2-chlorobenzyl mercaptan (0.02 mol) and metallic sodium (0.02 g atom) was subjected to the General Procedure to form Z-4-bromostyryl 2-chlorobenzylsulfide. The title compound was obtained in 84% yield following oxidation. $^1$HNMR (CDCl$_3$) δ 4.57 (2H, s), 6.70 (1H, d, $J_{H,H}$=11.58), 7.18–7.58 (8H aromatic+1H ethylenic).

EXAMPLE 16

Z-4-Bromostyryl 4-Fluorobenzylsulfone

A solution of 4-bromophenylacetylene (0.02 mol) and 4-fluorobenzyl mercaptan (0.02 mol) and metallic sodium (0.02 g atom) was subjected to the General Procedure to from Z-4-bromostyryl 4-fluorobenzylsulfide. The title compound was obtained in 78% yield following oxidation. $^1$HNMR (CDCl$_3$) δ 4.58 (2H, s), 6.65 (1H, d, $J_{H,H}$=11.78), 7.22–7.67 (8H aromatic+1H ethylenic).

EXAMPLE 17

Z-4-Methylstyryl Benzylsulfone

A solution of 4-methylphenylacetylene (0.02 mol) and benzyl mercaptan (0.02 mol) and metallic sodium (0.02 g atom) was subjected to the General Procedure to form Z-4-methylstyryl benzylsulfide. The title compound was obtained in 70% yield following oxidation. $^1$HNMR (CDCl$_3$) δ 2.48 (3H, s), 4.60 (2H, s), 6.68 (1H, d, $J_{H,H}$=11.94), 7.20–7.65 (9H aromatic+1H ethylenic).

EXAMPLE 18

Z-4-Methylstyryl 4-Chlorobenzylsulfone

A solution of 4-methylphenylacetylene (0.02 mol) and 4-chlorobenzyl mercaptan (0.02 mol) and metallic sodium (0.02 g atom) was subjected to the General Procedure to form Z-4-methylstyryl 4-chlorobenzylsulfide. The title compound was obtained in 74% yield following oxidation. $^1$HNMR (CDCl$_3$) δ 2.46 (3H, s), 4.64 (2H, s), 6.75 (1H, d, $J_{H,H}$=12.21), 7.18–7.57 (9H aromatic+1H ethylenic).

EXAMPLE 19

Z-4-Methylstyryl 2-Chlorobenzylsulfone

A solution of 4-methylphenylacetylene (0.02 mol) and 2-chlorobenzyl mercaptan (0.02 mol) and metallic sodium (0.02 g atom) was subjected to the General Procedure to form Z-4-methylstyryl 2-chlorobenzylsulfide. The title compound was obtained in 76% yield following oxidation. $^1$HNMR (CDCl$_3$) δ 2.50 (3H, s), 4.58 (2H, s), 6.80(1H, d, $J_{H,H}$=11.88), 7.20–7.63 (9H aromatic+1H ethylenic).

EXAMPLE 20

Z-4-Methylstyryl 4-Fluorobenzylsulfone

A solution of 4-methylphenylacetylene (0.02 mol) and 4-fluorobenzyl mercaptan (0.02 mol) and metallic sodium (0.02 g atom) was subjected to the General Procedure to form Z-4-methylstyryl 4-fluorobenzylsulfide. The title compound was obtained in 69% yield following oxidation. $^1$HNMR (CDCl$_3$) δ 2.46 (3H, s), 4.62 (2H, s), 6.78 (1H, d, $J_{H,H}$=11.98), 7.18–7.59 (9H aromatic+1H ethylenic).

EXAMPLE 21

Effect of Z-Styryl Sulfones on Breast, Prostate and Ovarian Tumor Cell Lines A. Cells.

The effect of the Z-styryl sulfones on normal fibroblasts and on tumor cells of breast, prostate and ovarian origin was examined utilizing the following cell lines: breast tumor cell lines: MCF-7, BT-20 and 435; prostate tumor cell lines LnCaP and DU-145; and ovarian tumor cell lines OVCAR and SKOV3. NIH/3T3 and HFL cells, which are normal murine and human fibroblasts, respectively, were also tested. LnCap is an androgen-dependent prostate tumor cell line. MCF-7 is an estrogen-responsive breast tumor cell line, while BT-20 and 435 are estrogen-unresponsive breast tumor cell lines. MCF-7, BT-20 and 435 were grown in Dulbecco's modified Eagle's medium (DMEM) containing 10% fetal bovine serum supplemented with penicillin and streptomycin. LnCaP and Du145 were cultured in RPMI with 10% fetal bovine serum containing penicillin and streptomycin. NIH3T3 and HFL cells were grown in DMEM containing 10% calf serum supplemented with penicillin and streptomycin. All cell cultures were maintained at 37° C. in a humidified atmosphere of 5% $CO_2$.

B. Treatment with Z-Styryl Sulfones and Viability Assay

Cells were treated with test compound at 2.5 micromolar concentration and cell viability was determined after 72 hours by the Trypan blue exclusion method. The results are set forth in Table 1.

Activity for each compound is reported as a range of cell induced death (% Death) with the lowest activity in the range of 10–20% and the highest being above 75%. For each compound tested, the activity was found to be in the same range for the three cell types.

Two of the twenty compounds tested (Examples 8 and 14) had kill rates of over 75%; three compounds (Examples 6, 10, and 16) had rates of 60–70%.

The five compounds exhibiting the highest activity contained halogen in the 4-position in Formula I.

Normal cells HFL and NIH 3T3 were treated with the same compounds in Table 1 under the same conditions of concentration and time. The normal cells were not killed.

TABLE 1

Effect of (Z)-styryl benzyl sulfones on tumor cells

| Ex. | $R_1$ | $R_2$ | $R_3$ | $R_4$ | Breast | Prostate | Ovarian |
|---|---|---|---|---|---|---|---|
| 1 | H | H | H | H | − | − | − |
| 2 | H | H | H | Cl | + | + | + |
| 3 | H | H | Cl | H | + | + | + |
| 4 | H | H | H | F | + | + | + |
| 5 | H | Cl | H | H | + | + | + |
| 6 | H | Cl | H | Cl | +++ | +++ | +++ |
| 7 | H | Cl | Cl | Cl | + | + | + |
| 8 | H | Cl | H | F | ++++ | ++++ | ++++ |
| 9 | H | F | H | H | + | + | + |
| 10 | H | F | H | Cl | +++ | +++ | +++ |
| 11 | H | F | Cl | Cl | + | + | + |
| 12 | H | F | H | F | ++ | ++ | ++ |
| 13 | H | Br | H | H | + | + | + |
| 14 | H | Br | H | Cl | ++++ | ++++ | ++++ |
| 15 | H | Br | Cl | Cl | + | + | + |
| 16 | H | Br | H | F | +++ | +++ | +++ |
| 17 | H | CH$_3$ | H | H | + | + | + |
| 18 | H | CH$_3$ | H | Cl | + | + | + |
| 19 | H | CH$_3$ | Cl | Cl | + | + | + |
| 20 | H | CH$_3$ | H | F | + | + | + |

The activity of the compounds at 2.5 micromolar after 72 hours.
Breast cell lines: MCF-7, BT-20, 435
Prostate cell lines: LnCaP, DU-145
Ovarian cell lines: OVCAR, SKOV3
10–20% Death = −
20–25% = +
40–50% = ++
60–70% = +++
above 75% = ++++

EXAMPLE 22

Effect of Z-Styryl Sulfones on Lung, Renal and Brain Tumor Cell Lines

The procedure of Example 21 was followed for certain of the (Z)-benzylsulfones, substituting the following cancer cell lines: lung, N417 and H157; renal, CAKI-1 and CAKI-2; glioma, U87 and SW1088. The results are set forth in Table 2.

TABLE 2

Effect of (Z)-styryl benzyl sulfones on tumor cells

| | | | | | Tumor cell type | | |
|---|---|---|---|---|---|---|---|
| Ex. | R₁ | R₂ | R₃ | R₄ | Lung | Renal | Glioma |
| 5 | H | Cl | H | H | + | + | + |
| 6 | H | Cl | H | Cl | +++ | +++ | +++ |
| 7 | H | Cl | Cl | Cl | + | + | + |
| 8 | H | Cl | H | F | ++++ | ++++ | ++++ |
| 10 | H | F | H | Cl | +++ | +++ | +++ |
| 11 | H | F | Cl | Cl | + | + | + |
| 12 | H | F | H | F | ++ | ++ | ++ |
| 14 | H | Br | H | Cl | ++++ | ++++ | ++++ |
| 15 | H | Br | Cl | Cl | + | + | + |
| 16 | H | Br | H | F | +++ | +++ | +++ |
| 18 | H | CH₃ | H | Cl | + | + | + |
| 20 | H | CH₃ | H | F | + | + | + |

The activity of the compounds at 2.5 micromolar after 72 hours.
Lung cell lines: N417, H157
Renal cell lines: CAKI-1, CAKI-2
Glioma cell lines: U87, SW1088
10–20% Death = –
20–25% = +
40–50% = ++
60–70% = +++
above 75% = ++++

All references cited with respect to synthetic, preparative and analytical procedures are incorporated herein by reference.

The present invention may be embodied in other specific forms without departing from the spirit or essential attributes thereof and, accordingly, reference should be made to the appended claims, rather than to the foregoing specification, as indication the scope of the invention.

What is claimed is:

1. A method of treating an individual for cancer comprising administering to said individual an effective amount of a compound according to the formula:

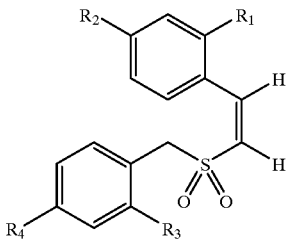

wherein

R₁ is selected from the group consisting of hydrogen, chloro and nitro;

R₂ is selected from the group consisting of hydrogen, lower alkyl, lower alkoxy, chloro, bromo, and fluoro; and R₃ and R₄ are independently selected from the group consisting of hydrogen, lower alkyl, nitro, chloro, bromo, and fluoro;

provided at least one of R₁ or R₂ is hydrogen,
wherein the cancer is selected from the group consisting of ovarian, breast, prostate, lung, renal and brain cancers.

2. A method for inducing apoptosis of tumor cells in an individual afflicted with cancer, comprising administering to said individual an effective amount of a compound according to the formula:

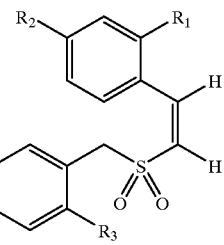

wherein

R₁ is selected from the group consisting of hydrogen, chloro and nitro;

R₂ is selected from the group consisting of hydrogen, lower alkyl, lower alkoxy, chloro, bromo, and fluoro; and R₃ and R₄ are independently selected from the group consisting of hydrogen, lower alkyl, nitro, chloro, bromo, and fluoro;

provided at least one of R₁ or R₂ is hydrogen,
wherein the tumor cells are selected from the group consisting of ovarian, breast, prostate, lung, renal and brain tumor cells.

3. A method according to claim 1 wherein

R₃ is hydrogen; and

R₂ and R₄ are independently selected from the group consisting of chloro, fluoro and bromo.

4. A method according to claim 2 wherein

R₃ is hydrogen; and

R₂ and R₄ are independently selected from the group consisting of chloro, fluoro and bromo.

5. A method according to claim 1 wherein the cancer is breast cancer.

6. A method according to claim 1 wherein the cancer is prostate cancer.

7. A method according to claim 2 wherein the tumor cells are breast tumor cells.

8. A method according to claim 2 wherein the tumor cells are prostate tumor cells.

9. A method according to claim 3 wherein the compound is Z-4-chlorostyryl 4-chlorobenzylsulfone.

10. A method according to claim 3 wherein the compound is Z-4-chlorostyryl 4-fluorobenzylsulfone.

11. A method according to claim 3 wherein the compound is Z-4-fluorostyryl 4-chlorobenzylsulfone.

12. A method according to claim 3 wherein the compound is Z-4-fluorostyryl 4-fluorobenzylsulfone.

13. A method according to claim 3 wherein the compound is Z-4-bromostyryl 4-chlorobenzylsulfone.

14. A method according to claim 3 wherein the compound is Z-4-bromostyryl 4-fluorobenzylsulfone.

15. A method according to claim 4 wherein the compound is Z-4-chlorostyryl 4-chlorobenzylsulfone.

16. A method according to claim 4 wherein the compound is Z-4-chlorostyryl 4-fluorobenzylsulfone.

17. A method according to claim 4 wherein the compound is Z-4-fluorostyryl 4-chlorobenzylsulfone.

18. A method according to claim 4 wherein the compound is Z-4-fluorostyryl 4-fluorobenzylsulfone.

19. A method according to claim 4 wherein the compound is Z-4-bromostyryl 4-chlorobenzylsulfone.

20. A method according to claim 4 wherein the compound is Z-4-bromostyryl 4-fluorobenzylsulfone.

21. A method of treating an individual for leukemia, comprising administering to said individual an effective amount of a compound according to the formula:

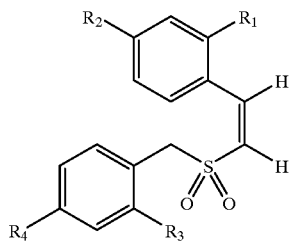

wherein $R_1$ is selected from the group consisting of hydrogen, chloro and nitro;

$R_2$ is selected from the group consisting of chloro, bromo, and fluoro;

$R_3$ is hydrogen; and $R_4$ is selected from the group consisting of chloro, bromo, and fluoro;

provided at least one of $R_1$ or $R_2$ is hydrogen.

22. The method of claim 21, wherein the compound is Z-4-fluorostyryl-4-chlorobenzyl sulfone.

* * * * *